United States Patent
Sumegi et al.

(10) Patent No.: US 6,306,878 B1
(45) Date of Patent: *Oct. 23, 2001

(54) PHARMACEUTICAL COMPOSITIONS CONTAINING HYDROXIMIC ACID DERIVATIVES

(76) Inventors: Balazs Sumegi, 7 Homokko utca, Pecs, H-7634, Budapest (HU); Peter Literati Nagy, 61/b Jablonka u., Budapest, H-1037 (HU); Laszlo Vigh, 9/A Kikindai u., Szeged, H-6726 (HU); Bruno Maresca, Via Vescovado 11, 80069 Vico Equense (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/722,499

(22) Filed: Sep. 27, 1996

(30) Foreign Application Priority Data

Sep. 29, 1995 (HU) .................................................. P9502843

(51) Int. Cl.$^7$ ................................................. A61K 31/445

(52) U.S. Cl. .................. 514/318; 514/237.2; 514/238.2; 514/255

(58) Field of Search .............................. 514/318, 238.2, 514/237.2, 255

(56) References Cited

U.S. PATENT DOCUMENTS 5,328,906 * 7/1994 Nagy et al. .
5,919,796 * 7/1999 Barabas et al. ....................... 514/318

* cited by examiner

*Primary Examiner*—Zohreh Fay
(74) *Attorney, Agent, or Firm*—Birch, Stewart, Kolasch & Birch, LLP

(57) ABSTRACT

The invention refers to pharmaceutical compositions suitable for the protection of the mitochondrial genom and/or mitochondrium from damages or for the treatment of diseases connected with such damages, said compositions comprising a hydroximic acid derivative of the formula:

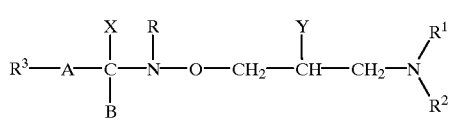

wherein
  $R^1$ represents a hydrogen or a $C_{1-5}$ alkyl group,
  $R^2$ stands for a hydrogen, a $C_{1-5}$ alkyl group, a $C_{3-8}$ cycloalkyl group or a phenyl group optionally substituted by a hydroxy or a phenyl group, or
  $R^1$ or $R^2$ together with the nitrogen atom they are attached to form a 5 to 8 membered ring optionally containing one or more further nitrogen, oxygen or sulfur atom(s) and said ring can be condensed with another alicyclic or heterocyclic ring, preferably a benzene, naphthalene, quinoline, isoquinoline, pyridine or pyrazoline ring, furthermore, if desired and chemically possible, the nitrogen and/or sulfur heteroatom(s) are present in the form of an oxide or dioxide,
  $R^3$ means a hydrogen, a phenyl group, a naphthyl group or a pyridyl group wherein said groups can be substituted by one or more halo atom(s) or $C_{1-4}$ alkoxy group(s),
  Y is a hydrogen, a hydroxy group, a $C_{1-24}$ alkoxy group optionally substituted by an amino group, a $C_{2-24}$ polyalkenyl-oxy group containing 1 to 6 double bond(s), a $C_{1-25}$ alkanoyl group, $C_{3-9}$ alkenoyl group or a group of the formula $R^7$—COO—, wherein $R^7$ represents a $C_{2-30}$ polyalkenyl group containing 1 to 6 double bond(s),
  X stands for a halo, an amino group, a $C_{1-4}$ alkoxy group, or
  X forms with B an oxygen atom, or
  X and Y together with the carbon atoms they are attached to and the —NR—O—CH$_2$ group being between said carbon atoms form a ring of the formula

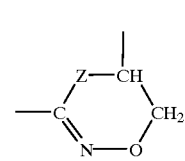

wherein
  Z represents an oxygen or a nitrogen,
  R stands for a hydrogen or
  R forms with B a chemical bond,
  A is a $C_{1-4}$ alkylene group or a chemical bond or a group of the formula

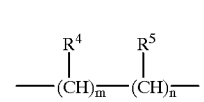

wherein
  $R^4$ represents a hydrogen, a $C_{1-5}$ alkyl group, a $C_{3-8}$ cycloalkyl group or a phenyl group optionally substituted by a halo, a $C_{1-4}$ alkoxy group or a $C_{1-5}$ alkyl group,
  $R^5$ stands for a hydrogen, a $C_{1-4}$ alkyl group or a phenyl group,
  m has a value of 0, 1 or 2,
  n has a value of 0, 1 or 2,
or a pharmaceutically acceptable acid addition salt thereof as the active ingredient.

7 Claims, No Drawings

PHARMACEUTICAL COMPOSITIONS CONTAINING HYDROXIMIC ACID DERIVATIVES

The invention refers to pharmaceutical compositions suitable for the protection of the mitochondrial genom and/or mitochondrium from damages or for the treatment of diseases connected with such damages, said compositions comprising a hydroximic acid derivative of the formula

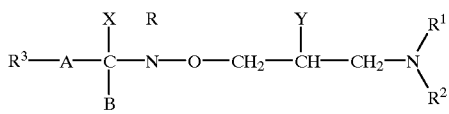
I wherein
- $R^1$ represents a hydrogen or a $C_{1-5}$ alkyl group,
- $R^2$ stands for a hydrogen, a $C_{1-5}$ alkyl group, a $C_{3-8}$ cycloalkyl group or a phenyl group optionally substituted by a hydroxy or a phenyl group, or
- $R^1$ and $R^2$ together with the nitrogen atom they are attached to form a 5 to 8 membered ring optionally containing one or more further nitrogen, oxygen or sulfur atom(s) and said ring can be condensed with another alicyclic or heterocyclic ring, preferably a benzene, naphthalene, quinoline, isoquinoline, pyridine or pyrazoline ring, furthermore, if desired and chemically possible, the nitrogen and/or sulfur heteroatom(s) are present in the form of an oxide or dioxide,
- $R^3$ means a hydrogen, a phenyl group, a naphthyl group or a pyridyl group wherein said groups can be substituted by one or more halo atom(s) or $C_{1-4}$ alkoxy group(s),
- Y is a hydrogen, a hydroxy group, a $C_{1-24}$ alkoxy group optionally substituted by an amino group, a $C_{2-24}$ polyalkenyloxy group containing 1 to 6 double bond(s), a $C_{1-15}$ alkanoyl group, a $C_{3-9}$ alkenoyl group or a group of the formula $R^7$—COO—, wherein $R^7$ represents a $C_{2-30}$ polyalkenyl group containing 1 to 6 double bond(s),
- X stands for a halo, an amino group, a $C_{1-4}$ alkoxy group, or
- X forms with B an oxygen atom, or
- X and Y together with the carbon atoms they are attached to and the —NR—O—CH$_2$ group being between said carbon atoms form a ring of the formula

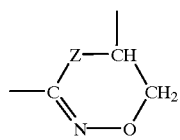
a wherein
- Z represents an oxygen or a nitrogen,
- R stands for a hydrogen or
- R forms with B a chemical bond,
- A is a $C_{1-4}$ alkylene group or a chemical bond or a group of the formula

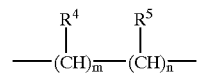
b wherein
- $R^4$ represents a hydrogen, a $C_{1-5}$ alkyl group, a $C_{3-8}$ cycloalkyl group or a phenyl group optionally substituted by a halo, a $C_{1-4}$ alkoxy group or a $C_{1-5}$ alkyl group,
- $R^5$ stands for a hydrogen, a $C_{1-4}$ alkyl group or a phenyl group,
- m has a value of 0, 1 or 2,
- n has a value of 0, 1 or 2, or a pharmaceutically acceptable acid addition salt thereof as the active ingredient.

HU-P No. 177 578 and its equivalent U.S. Pat. No. 4,308,399 describe hydroximic acid derivatives within the compounds of the formula I suitable for the treatment of diabetic angiopathy.

HU-P No. 207 988 and its equivalent E-P No. 417 210 also describe hydroximic acid halogenides within the formula I having a selective beta-blocking effect, thus, being suitable for the treatment of diabetic angiopathy.

HU-P Application No. 2385/92 published under No. T/66350 describes further hydroximic acid derivatives within the formula I. These known compounds can be used in the treatment of vascular deformations, mainly in the therapy of diabetes mellitus.

It is well-known that the nuclear genom of a human cell encodes about 100 000 genes, but in the cytoplast there is also a small, independent mitochonrial genom/Wellace, D. C., Science, 256, 628–632 (1992)/.

The mitochondrial genom codes only for 13 genes/Clayton, D. A., Cell, 28, 693–705 (1982)/, but without them the cell is unable to consume the oxygen, therefore, as an effect of the damages in the mitochondrial genom, the cell becomes anaerobic. Unlike the nuclear genom, the mitochondrial genom does not have a DNA repair capacity and the mitochondrial DNA (mtDNA) is not surrounded by histons which makes the mitochondrial genes much more vulnerable than the nuclear encoded genes/Tzagoloff, A., Myer, A. M., Annu. Rev. Biochem., 55, 249–285 (1986)/. More than 90% of the oxygen consumption of a cell takes place in the mitochondrial inner membrane where besides normal oxidation also oxygen free radicals are formed /Stryer, L., Biochemistry, 4th edition, W. H. Freeman and Co., New York, 1995/. Such free radicals can easily modify the mitochondrial DNA in the immediate vicinity of their formation. The formation of the reactive oxygen free radicals significantly increases e.g. during the reoxigenation following an ischaemia which increased free radical concentration may cause considerable and irreversible damages to the mitochondrial DNA /Markhund, S. L., J. Mol. Cell. Cardiol., 20, (Supplement II), 23–30 (1988)/. Even under normal circumstances, free radicals cause minor but accumulative damages to the mtDNA. Therefore it is understandable that the damages of mtDNa increase by age /Wellace, D. C., Annu. Rev. Biochem., 61, 1175–1212 (1992)/, although the level of such damages depends on the individual, and that such damages of mtDNA may well cause the development of cardiomyopathy and neurodegenerative diseases in elderly people /Cortopassi, G. A., Arnheim, N., Nucleic Acids Res., 18, 6027–6033 (1990)/.

Through damages of the energy metabolism of a cell, the damages of the mitochondrial genom can cause severe illnesses such as myopathy /Luft, R., Proc. Natl. Acad. Sci. USA, 91, 8731–8738 (1994)/, dilatative or hypertrofic cardiomyopathy /Ozawa, T. et. al., Biochem. Biophys. Res. Commun., 170, 830–836 (1990)/, furthermore may have a role in the aggravation by age of a number of neurodegenerative diseases (such as Parkinson's disease, Huntington's disease, Alzheimer's disease) and of the severe symptoms of diabetes /Luft, R., cited publication/.

In a number of the above diseases (e.g. the myopathy), a treatment with antioxidants was applied (treatment with coenzyme Q and vitamin C) /Shoffner, J. M., Wallace, D. C., Adv. Hum. Genet., 19, 267–330 (1990)/. These treatments bring results only occasionally. Further test treatments were made to avoid damages of after-ischaemia reoxidation applying antioxidant and metabolic therapy, using lipoamid. Lipoamid corrects the damages to the heart caused by the ischaermia on one hand by its antioxidant effect, on the other hand by its positive influence on the mitochondrial metabolish /Sümegi, Balazs et al., Biochem. J., 297, 109–113 (1994)/. Without a profound knowledge of the damaging process, no breakthrough therapy has been developed yet.

Based on the above, there is a need for the development of a pharmaceutical product which can protect the mitochondrial genom from damages or also prevent such damages.

It was found that the compounds of the formula I are able to protect the mitochondrial genom from damages, thus, they are suitable for the protection of the mitochonrial genom and/or mitochondrium from damages or for the treatment of diseases connected with such damages. Examples of diseases of mitochondrial origin:

| KSS | (Kearns-Sayre's syndrome), |
|---|---|
| MERRF | (myoclonus epilepsy and ragged red fibers syndrome), |
| LHON | (Leber's hereditary optic neuropathy), |
| MELAS | (mitochondrial myopathy, encephalopathy, lactic acidosis and stroke-like episodes), |
| Leigh disease, CPEO, | (chronic progressive external phthalmoplegia), |
| Alper's syndrome. | |

Examples of age-dependent degenerative diseases where the mitochondrial genom has been damaged:

| Neurodegenerative diseases: | |
|---|---|
| Alzheimer's disease, | |
| Parkinson's disease, | |
| ALS | (amyotrophic lateral sclerosis), |
| HD | (Huntington's disease), |

Cardiomiopathies and other myopathies.

Thus, the invention refers to pharmaceutical compositions comprising 0.1 to 95% by mass of a hydroximic acid derivative of the formula I or a pharmaceutically acceptable acid addition salt thereof as the active ingredient in admixture with one or more conventional carrier(s).

In the specification and Claims, a $C_{1-5}$ alkyl group is, for example, a methyl, ethyl, n-propyl, isorpopyl, n-butyl or n-pentyl group, preferably a methyl or an ethyl group.

A $C_{3O8}$ cycloalkyl group is, for example, a cyclopropyl, cyclopentyl, cyclohexyl, cycloheptyl or cyclooctyl group, preferably a cyclopentyl or a cyclohexyl group.

A 5 to 8 membered ring containing one or more heteroatom(s) can be, for example a pyrrole, pyrazole, imidazole, oxazole, thiazole, pyridine, pyridazine, pyrimidine, piperazine, morpholine, indole, quinolime etc. ring.

A $C_{1-24}$ alkoxy group is, for example, a methoxy, ethoxy, n-propoxy, tert-butoxy, n-pentoxy, decyloxy, dodecyloxy, octadecyloxy etc. group.

A $C_{1-25}$ alkanoyl group is, for example, a formyl, acetyl, propionyl, butiryl, caproyl, palmityl, stearyl etc. group.

A $C_{3-9}$ alkenoyl group is, for example, an acryloyl, pentenoyl, hexenoyl, heptenoyl, octenoyl etc. group.

a $C_{1-4}$ alkylene group is, for example, a methylene, ethylene, propylene or butylene group.

A halo atom is, for example, a fluoro, chloro, bromo or iodo atom, preferably a chloro or a bromo atom.

If Y stands for a group of the formula $R^7$—COO—, it can represent, for example, a limolenoyl, linoloyl, docosahexanoyl, eicosapentanoyl, arachidonoyl etc. group.

The pharmaceutically acceptable acid addition salts of the compounds of the formula I are the acid addition salts formed with pharmaceutically acceptable inorganic acids such as hydrochloric acid, sulfuric acid etc. or with pharmaceutically acceptable organic acids such as acetic acid, fumaric acid, lactic acid etc.

A preferred subgroup of the compounds of the formula I consists of the hydroximic acid derivatives of the formula

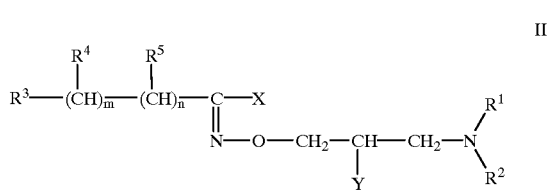

II wherein $R^1$, $R^2$, $R^3$, $R^4$, $R^5$, m and n are as stated in relation to formula I, X represents a halo atom or an amino group, Y means a hydroxy group.

Especially preferred compounds of the formula II are those wherein $R^1$ and $R^2$ together with the nitrogen atom they are attached to form a piperidino group, $R^3$ stands for a pyridyl group, m and n have a value of 0, X is as defined above. Of these compounds, preferred species are as follows:

0-(3-piperidino-2-hydroxy-1-propyl)pyrid-3-ylhydroximic acid chloride (Compound "A") and 0-(3-piperidino-2-hydroxy-1-propyl)nicotinic amidoxime (compound "B").

A further preferred subgroup of the hydroximic acid derivatives of the formula I consists of the compounds of the formula

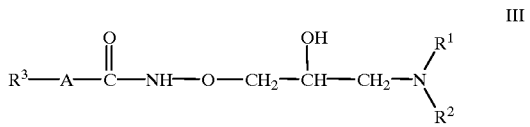

III wherein $R^1$, $R^2$, $R^3$ and A are as stated in relation to formula I.

Another preferred subgroup of the hydroximic acid derivatives of the formula I consists of the compounds of the formula

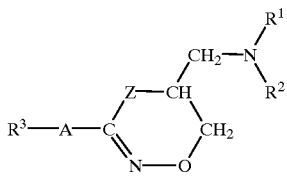

wherein $R^1$, $R^2$, $R^3$ and A are as stated in relation to formula I, Z represents an oxygen or a nitrogen atom.

A still further preferred subgroup of the hydroximic acid derivatives of the formula I consists of the compounds of the formula

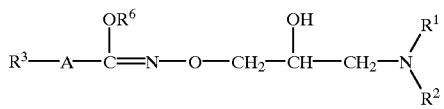

wherein $R^1$, $R^2$, $R^3$ and A are as stated in relation to formula I, $R^6$ stands for a $C_{1-4}$ alkyl group.

The compounds of the formula I can be prepared by the processes known from HU-P Nos. 177 578 and 207 988 as well as from HU-P Application published under No. T/66350.

The pharmaceutical composition of the invention comprises 0.1 to 95% by mass, preferably 1 to 50% by mass, especially 5 to 30% by mass, of a hydroximic acid derivative of the formula I or a pharmaceutically acceptable acid addition salt thereof as the active ingredient and one or more conventional carrier(s).

The pharmaceutical compositions of the invention are suitable for peroral, parenteral or rectal administration or for local treatment, and can be solid or liquid.

The solid pharmaceutical compositions suitable for peroral administration may be powders, capsules, tablets, film-coated tablets, microcapsules etc., and can comprise binding agents such as gelatine, sorbitol, poly(vinylpyrrolidone) etc.; filling agents such as lactose, glucose, starch, calcium phosphate etc.; auxiliary substances for tabletting such as magnesium stearate, talc, poly(ethyleneglycol), silica etc.; wetting agents such as sodiumlaurylsulfate etc. as the carrier.

The liquid pharmaceutical compositions suitable for peroral administration may be solutions, suspensions or emulsions and can comprise e.g. suspending agents such as gelatine, carboxymethylcellulose etc.; emulsifiers such as sorbitane monooleate etc.; solvents such as water, oils, propyleneglycol, ethanol etc.; preservatives such as methyl p-hydroxybenzoate etc. as the carrier.

Pharmaceutical compositions suitable for parenteral administration consist of sterile solutions of the active ingredient, in general.

Dosage forms listed above as well as other dosage forms are known per se, see e.g. Remington's Pharmaceutical Sciences, 18th Edition, Mack Publishing Co., Easton, USA (1990).

The pharmaceutical compositions of the invention contain, generally, unit dosage. A typical daily dose for adult patients amounts to 0.1 to 1000 mg of the compound of the formula I or a pharmaceutically acceptable acid addition salt thereof. The above dose can be administered in one portion or in more portions. The actual dose depends on many factors and is determined by the doctor.

The pharmaceutical compositions of the invention are prepared by admixing a compound of the formula I or a pharmaceutically acceptable acid addition salt thereof to one or more carrier(s), and converting the mixture obtained to a pharmaceutical composition in a manner known per se. Useful methods are known from the literature, e.g. Remington's Pharmaceutical Sciences.

A further embodiment of the invention consists of a method for the protection of the mitochondrial genom and/or mitochondrium from damages which comprises administering an effective non-toxic dose of a compound of the formula I, wherein R, $R^1$, $R^2$, $R^3$, X, Y, A and B are as stated in relation to formula I, or a pharmaceutically acceptable acid addition salt thereof to a patient liable to such damages. Thus, in accordance with the invention, the compound of the formula I can be used as a preventive tool to avoid damages of the mitochondrial genom and/or mitochondrium.

A still further embodiment of the invention consists of a method for the treatment of diseases connected with the damage of the mitochondrial genom and/or mitochrondrium which comprises administering an effective non-toxic dose of a compound of the formula I, wherein R, $R^1$, $R^2$, $R^3$, X, Y, A and B are as stated in relation to formula I, or a pharmaceutically acceptable acid addition salt thereof to a patient suffering from said diseases.

As mentioned in an earlier part of the description, the method of the invention is directed especially for the treatment of myopathy and/or cardiomypathy as well as neurodegenerative diseases such as Alzheimer's disease, Parkinson's disease or Huntington's disease.

According to a preferred method of the invention, a hydroximic acid derivative of the formula II, wherein $R^1$, $R^2$, $R^3$, $R^4$, $R^5$, X, Y, m and n are as stated in relation to formula II, or a pharmaceutically acceptable acid addition salt thereof is administered.

In accordance with a still preferred method of the invention, a compound of the formula II, wherein $R^1$ and $R^2$ together with the nitrogen atom they are attached to form a piperidino group, m and n have the value of 0, X and Y are as stated in relation to formula II, or a pharmaceutically acceptable acid addition salt thereof is administered.

According to an especially preferred method of the invention, 0-(3-piperidino-2-hydroxy-1-propyl)pyrid-3-yl-hydroximic acid chloride or 0-(3-piperidino-2-hydroxy-1-propyl)-nicotinic amidoxime or a pharmaceutically acceptable acid addition salt thereof is administered.

In Vitro Tests

The mitochondrial genom protection effect of the hydroximic acid derivatives of the formula I was tested by their ability to protect the oxidative phosphorylation, in vitro. The theoretical background of the tests is that the energy needed for the cells is produced by the adenozin-triphosphate (ATP) which is synthesized in the mitochondrium. The abnormalities of the substrate transport, the citrate pathwax, the defect the respiratory complexes and a disconnect in the oxidative phosphorylation entails a disturbed energy supply of the cell. In the test the oxidative phosphorylation was damaged by applying heat-shock on *Sacharomyces cerevisiae* yeast cells and K562 human eritroleukemic cells and the protective effect of compound "B" was determined.

It is known that one of the damaging effects of the heat-shock that is developed immediately, i.e. within a few minutes, affects the mitochondrium by disconnecting the respiratory chain from the oxidative phosphorylation. Tests using chemical uncouplers showed that protons pumped into the space between the inner and outer mitchondrium membranes by the enzyme complexes of the respiratory chain during electron transport get back to the inner space due to the effect of the uncouplers, thus, no ATP is synthesized. Due to heat-shock, there is a similar process going on which results in a rapidly decreasing energy supply to the cells.

Materials Used in Testing

*Sacharomyces cerevisiae* cell culture. The S288C haploid wild-type cell line was cultured on a YPG medium that contained 1% of yeast extract, 2% of peptone and 3% of glycerol. The culture was shaken on a liquid medium in a water bath at 25° C. under aerobic conditions.

The K562 Culture

The K562 eritroleukemic type cell line of human chronic myeloid leukemic origin was cultured on an RPMI 1640 liquid medium in the presence of 10% of calf serum, at a temperature of 37° C., in a wet gas mixture containing 95% of air and 5% of carbon dioxide.

Oligomycin

Carbonylcyanide m-chlorophenylhydrazone (CI-CCP) manufacturer, Sigma Chemicals Co., St. Louis, USA).

Oxygen consumption was measured in the following way:

The cells were centrifuged during their logarithmic growth phase and, in case of the *Sacharomyces cerevisiae*, were taken in a tenfold amount of YPG medium containing 1% of mannose instead of the 2% of glycerol. In case of the K 562, after the separation, the cells were taken in a $4 \times 10^6$ cell/ml concentration in an RPMI 1640 medium containing 20 mM of HEPES. The oxygen consumption was measured in a 2 ml thermostated cuvet, with Clare's electrode. Details of the method are described in the following article: Patriarca, E. J. and Maresca, B. Experimental Cell Research, 190, 57–64 (1990). Stimulation of the respiratory rate is given in % using the formula:

$$[(V^{CI-CCP}/V^{Olig})-1] \times 100$$

One hour before the heat-shock, after the separation, $10^{-5}$, $2.5 \times 10^{-5}$, $5 \times 10^{-5}$ M of compound "B" and solvent (PBS i.e. physiological sodium chloride solution containing phosphate buffer), respectively, were added to the medium. The heat-shock was carried out by keeping the culture at 42° C. for 5 minutes instead of the original temperature of 25° C. In case of the K562 cells the culture was kept at 48° C. for 10 minutes instead of the original 37° C.

It has been noted during the experiments that the heat-shock significantly uncoupled the electron transport chain from the ATP synthesis in both the *Sacharomyces cerevisiae* and K 562 cells.

The results obtained are shown in Tables 1 and 2 where the method of treatment is displayed together with the stimulation in % and the obtained protection in %.

TABLE 1

Protection of the oxidative phosphorylation of *Sacharomyces cerevisiae*

| Treatment | Stimulation, % | Protection, % |
|---|---|---|
| 25° C. | 99 ± 13 | |
| 42° C. + solvent | 8 ± 2 | 0 |
| 42° C. + 1 × 10⁻⁵M compound "B" | 33 ± 5 | 27 |
| 42° C. + 2.5 × 10⁻⁵M compound "B" | 47 ± 4 | 43 |
| 42° C. + 5 × 10⁻⁵M compound "B" | 43 ± 5 | 38 |

TABLE 2

Protection of the oxidative phosphorylation of the K 562

| Treatment | Stimulation, % | Protection, % |
|---|---|---|
| 37° C. | 117 ± 22 | |
| 48° C. + solvent | 27 ± 3 | 0 |
| 48° C. + 1 × 10⁻⁵M compound "B" | 70 ± 8 | 36 |
| 48° C. + 2.5 × 10⁻⁵M compound "B" | 95 ± 11 | 57 |
| 48° C. + 5 × 10⁻⁵M compound "B" | 97 ± 11 | 58 |

Data of Tables 1 and 2 demonstrate that the application of compound "B" undoubtedly provided an increased protection to the cells by preventing the uncoupling of the mitochondrial respiratory complexes.

In the examined range, the optimal concentration of the compound "B" was 25 micromoles. In addition to retaining the proper cell functions, most probably indirectly prevents the formation of oxygen free radicals. From this we can conclude that the compound "B" provides protection against damages of the mitochondrial genom.

Protection of the mitochondria from heat induced uncoupling

Under normal circumstances the respiratory complexes pump out proton during the oxidation of NADH creating a proton gradient in the two sides of the inner mitochondrial membrane. This proton gradient provides energy to ATP synthesis from ADP and inorganic phosphate. The protons can only reenter the inner membrane space through $F_1F_o$ATPase utilizing the energy of proton gradient for ATP synthesis from ADP and inorganic phosphate (Pi). In the absence of ADP or Pi, the proton gradient increases and inhibits the respiratory complexes and the mitochondrial oxygen consumption. However, if there is any damage in the inner membrane, the protons can reenter the inner membrane space through the damaged region, and the energy of proton gradient is not utilized by $F_1F_o$ATPase, and so the mitochondrial oxidation becomes ADP independent (mitochondria becomes uncoupled.)

It is well known that heat-stress can induce an uncoupling of mitochondrial oxidation from mitochondrial energy (ATP) production which is the consequence of heat-stress induced mitochondrial inner membrane damage. In the damaged membrane regions, protons leak back from the intermembrane space to innermembrane compartment, thus, the mitochondrial oxidation becomes ADP independent.

For the test, mitochondria were isolated from control rats or from rats treated with 40 mg/kg of compound "B" 6 hours before preparation, the preparation taking place as described by Sumegia et al., J. Biol. Chem. 259, 8748 (1984). Oxygen consumption was determined with Clark electrode in a chamber at 37° C. The rate of oxygen consumption in the presence of 5 mM of ADP as well as in the absence of ADP is determined and shown in Table 3 both for untreated mitochondria and mitochondria preincubated for 8 minutes at 42° C.

TABLE 3

Protection of the mitochondria from heat induced uncoupling

| | Treatment | |
|---|---|---|
| | None | 8 min. at 43° C. |
| Mitochondria | Ratio of mitochondrial oxygen consumption in the presence versus in the absence of ADP | |
| Control animals | 6 ± 0.8 | 2.7 ± 1.1 |
| Compound "B" treated animals | 6.2 ± 1.0 | 5.0 ± 1.2 |

Data shown are the average+standard error of three experiments.

It can be seen in Table 3 that under normal conditions, the mitochondrial oxidation is approximately 6 times faster in the presence of ADP than in ADP free medium showing a good coupling between mitochondrial oxidation and ATP synthesis. However, heat-stress significantly decreases the coupling of mitochondria, and in the control cases this value decreased (2.7) but in the mitochondria from animals pretreated with compound "B" still preserved a relatively high coupling ratio (5.1). These data show that the compounds of the formula I and especially compound "B" protected the mitochondrial energy production (ATP synthesis) from heat-stress caused damage.

Protection of cholinergic neurons from hydrogen peroxide induced cell degeneration It is well known that hydrogen peroxide causes oxidative cell damage through generating oxygen related free radicals in cells. Therefore, hydrogen peroxide induced cell damage can be used as a general model for neuron degeneration. SN6. 10.2.2 hybrid, N18TG2 —ED15 septal neurons cell-line /Hammond et al., Science, 234, 1237 (1986)/ were used to study the protecting effect of the compounds of the formula I against oxygen related free radical caused cell damage which is the main pathway in most nuerodegenerative diseases.

For the test, the cells were divided into two groups on 96-wells plate. One of the groups was maintained in the medium containing compound "B" (40 mg/l), another one was maintained in the base medium. The treatment was started 24 hours after dividing. Both of the groups were treated with their medium containing different concentrated of hydrogen peroxide. The survival test was performed after 48 hours treatment periods.

Survival test:

The medium was removed from the well, the cells were rinsed with sterile PBS and then 150 μg of alkaline phosphatase substrate dissolved in 150 μg of fresh diethanolamine buffer (pH 9.8) was added to each well. Plates were incubated at 30° C. and the reaction was stopped by adding 50 μl of sodium hydroxide to each well. The absorbance was measured at 405 nm by Dynatech ELISA reader and, peripheral wells of each plate containing only medium were utilized for blank background determination.

The results obtained are shown in Table 4.

TABLE 4

Protection of cholinergic neurons from hydrogen peroxide induced cell lysis by compound "B"

| | Medium | Medium with compound "B" |
|---|---|---|
| control | 100% | 100% |
| 60 mM $H_2O_2$ | 11 ± 2% | 63 ± 4% |
| 120 mM $H_2O_2$ | 8 ± 3% | 52 ± 5% |

Table 4 shows that the compound of the formula I tested (i.e. compound "B") effectively protects cholinergic neurons from hydrogen peroxide induced cell lysis. Since hydrogen peroxide kills cell by generating a large quantity of oxygen related free radical, compound "B" can protect neurons in any diseases where neuronal damage is associated with oxygen related free radicals. Therefore, compounds of the formula I can be advantageous in Parkinson's disease, Amyotrophic Lateral Sclerosis (ALS), Huntingdon's disease and several dementia of mixed orgin /Life Scienses, 56, 1151–1171 (1995)/.

In vivo tests the mitochondrial genome protective effect of the hydroximic acid derivatives of the formula I was also tested in vivo, treating rats. Vistar rats were treated daily with AZT (3'-azidothymidine, manufacturer: Sigma Chemicals Inc.) in a dose of 50 mg/kg for 14 days. Certain test groups were treated with AZT in combination either with the compound "A" (daily dose of 20 mg/kg) or with the compound "B" (daily dose of 40 mg/kg). During and after the treatment various measurements were made.

1) Schiller AT-6 ECG was used to monitor cardiac function of the animals on all four limbs. The ECG parameters were evaluated using a standard method described in the technical literature /Kawai, C., Takatso, T., New Engl. J. Med., 293, 592 (1965), Angelakos, E. T., Bernardina, P. J. Appl. Physiol., 18, 261–263 (1963)/. We have determined the RR, PR and TQ intervals and the J point depressions. The results obtained are shown in Table 5 where values are presented as the average of 5 measurements with ±standard deviation.

TABLE 5

Effect of compound "B" on the AZT induced cardiac function abnormalities (cardiomyopathies)

| Treatment | RR | PR | QT (ms) | J (mm) |
|---|---|---|---|---|
| Before treatment | 174 ± 12 | 53 ± 2 | 70 ± 2 | −0.1 ± 0.1 |
| Treatment for 14 days with daily 50 mg/kg of AZT | 284 ± 16 | 82 ± 3 | 112 ± 9 | −1.1 ± 0.1 |
| Treatment for 14 days with daily 50 mg/kg of AZT and 40 mg/kg of compound "B" | 161 ± 24 | 47 ± 6 | 76 ± 5 | −0.2 ± 0.14 |

Data of Table 5 demonstrate that as an effect of the AZT treatment, compared to the control group, the animal heart frequency was significantly prolonged (RR) and also the PQ intervals were increased. Furthermore, the QT value increased significantly and in leads I and VL which represent the main muscle mass of the left ventricle, significant J point depression (pver 0.1 mV) were found. These parameters characterize a developed myocardial ischaemia or a defective oxygen consumption. However, in cases when, in addition to AZT, also compound "B" was administered to the rats in a daily dose of 40 mg/kg, the heart parameters returned to the normal range, that is the compound protected the heard from the abnormalities induced by AZT.

2) The respiratory activity of the animals was determined. In doing so the activities of the NADH: cytochrome C oxidoreductase, cytochrome oxidase and citrate synthase were determined with methods described in the technical literature /Sitmegi, Balazs et aL; Clin. Chim. Acta., 192, 9–18, (1990)/. (NADH: nicotinic acid adenine dinucleotid, reduced form). The result obtained are shown in Table 6.

TABLE 6

Effects of compounds "A" and "B" on the AZT induced decrease in the respiratory activity

| Treatment | unit/gram wet tissue | | |
| --- | --- | --- | --- |
| | Cytochrome oxidase | NADH: cytochrome C oxidoreductase | Citrate synthase |
| Control group | 14.7 ± 1.6 | 11.6 ± 0.7 | 292 ± 28 |
| AZT | 8.7 ± 2 | 9.5 ± 0.2 | 242 ± 19 |
| AZT + compound "A" | 10.3 ± 1.2 | 11.3 ± 0.5 | 262 ± 47 |
| AZT + compound "B" | 11.8 ± 1.3 | 10.5 ± 1 | 271 ± 11 |

It is well demonstrated in Table 6 that AZT treatment significantly decreases the activity of the respiratory complexes in the mitochondria of the heart. In this way, AZT remarkably reduces the oxidative energy production in the heart which can lead to a state in that the heart is unable to properly perform its basic function (see Table 5, ECG data). Besides this, a decreased capacity of the mitochondrial, respiration can lead to an abnormal mitochondrial metabolism which may cause further heart damages.

When AZT was administered to animals in combination with the compound "A" or "B", its respiratory activity decreasing effect almost disappeared and the respiratory activity values stayed close to normal. That is the tested compounds of the formula I significantly decreased the AZT induced mitochondrial membrane damages by protecting the respiratory complexes.

3) The damages to the mitochondrial genome were examined. Damages to the mitochondrial genome were determined applying the PCR method. (PCR: plimerase chain reaction). The primers were selected by amplifying the range from the cytochrome oxidase component I to the cytochrome B in order to look for deletions: (The primers were purchased from the Ransonhill BioScience Co. ). The method applied is described in the publication of Sumegi, Balazs et. al. B.B.A. (1996)/ which publication is being edited. Using PCR primers in amplifying the region 4929 to 16298 of the mitochondrial genome showed that 0.5 and 1.5 kb ranges significantly amplified in AZT treated rats. At the same time, no amplification of such short ranges is seen on the animals of the control group. It is understandable that an undamaged genom does not amplifiy short DNA ranges as in these tests the primers are more than 11.3 kb from each other. The fact that such short DNA ranges are amplified in AZT treated rats shows that, due to the AZT treatment, 10 kb ranges are deleted from the mitochondrial genom and it is in such damaged genoms that the primers become as close to each other as 0.5–1.5 kb. As a consequence, the DNA range can be amplified. The amplification of such DNA ranges shows the damage to the mitochondrial genom, that is the partial or complete deletion of the genes coding for the subgroups I, II and III of the cytochrome oxidase, of the genes encoding for ATP 6 to 8, the genes coding for Complex I or NADH: ubiquinone oxidoreductase 2, 4 4L, 5 and 6, and coding for cytochrome B.

When AZT was administered to animals in combination with compound "B", the amplification of the above short DNA ranges have significantly decreased and certain DNA fragments could not be detected.

This means that compound "B" protected the above genes from AZT induced damages or at least significantly decreased those damages. It is to be noted that the AZT induced artifical damages to the above genes can also occur as an effect of ischaemic cardiomyopathy or cardiomyopathy of aged people.

The effect of the compund of the formula I on inherited mitochondrial cardiomyopathies.

Test were carried out using inherited mitochondrial cardiomyopathic rats that were treated with a daily dose of 40 mg/kg of compound "B" for 14 days. The rat heart function was monitored by ECG. The EGC data obtained for the control group and the group treated with compound "B" are shown in Table 7. Values are presented as the average of 3 measurements with ±standard deviation.

TABLE 7

The effect of compound "B" on the heart function of rats with inherited mitochondrial cardiomyopathy

| Treatment | RR | PR | QT (ms) | J (mm) |
| --- | --- | --- | --- | --- |
| Control group | 204 ± 20 | 54 ± 5 | 92 ± 8 | −1.0 ± 0.1 |
| Compound "B" | 169 ± 21 | 43 ± 7 | 71 ± 7 | −0.3 ± 0.1 |

Tests were performed on rats with inheritied cardiomyopathy which have adnormal heart funcitons. This fact can easily be seen from Table 7. These cardiomyopathic rats serve as a perfect model of ischaemic cardiomyopthy and cardiomyopathy of aged people. As an effect of the 14 days' treatment with compound "B", the animals' heart functions improved significantly and theECG parameters moved back to the normal range.

The above tests show that the hydroximic derivatives of the formula I are able to protect the mitochondrial genom against various damages. In the case of the animal modes used, they have virtually eliminated the AZT induced heart damages and this can bear a great significance in the human medical science considering that, at present, more than a hundred thousand people are treated with AZT worldwide.

Further important feature of the compounds is that in case of a developed cardiomyopathy (where the mitochondrial damages are similar to those of the ischaemic cardiomyopathy and the cardiomyopathy of aged people), they elimanate heart function abnormalities and restore the normal ECG parameters.

Based on the above tests it can be said that the pharmaceutical compositions of the invention containing as active ingredient a compound of the formula I can protect the mitochondrial genom or the mitochomdrium from damages, furthermore can treat diseases with already developed damages of that kind.

What is claimed is:

1. A method for the protection of the mitochondrial genome and/or mitochondrium from damage leading to myopathies and nuerodegenerative diseases, which comprises administering an effective non-toxic dose to a patient susceptible to such damage of an amidoximic acid derivative of formula I

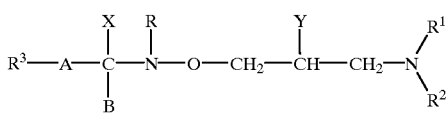

wherein
$R^1$ represents a hydrogen atom or a $C_{1-5}$ alkyl group,
$R^2$ represents for a hydrogen atom, a $C_{1-5}$ alkyl group, a $C_{5-7}$ cycloalkyl group, or
$R^1$ and $R^2$ together with the nitrogen atom they are attached to form a 5 to 8 membered ring optionally containing one or more further nitrogen or oxygen atom(s) and said ring can be condensed with a benzene ring,
$R^3$ represents a hydrogen atom, a phenyl group, a naphtyl group or a pyridyl group wherein said groups can be substituted by one or more halo atom(s) or $C_{1-4}$ alkoxy groups(s),
Y is a hydroxy group,
X represents an amino group,
R forms with B a chemical bond,
A is a group of the formula b

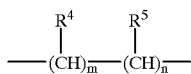

wherein
$R^4$ represents a hydrogen atom,
$R^5$ represents a hydrogen atom,
m has a value of 0, 1 or 2,
n has a value of 0, 1 or 2, or a pharmaceutically acceptable acid addition salt thereof.

2. The method of claim 1, wherein $R^1$ and $R^2$ together with a nitrogen atom are attached to form a piperidiono group.

3. The method of claim 1, wherein the hydroximic acid derivative is O-(3-piperidino-2-hydroxy-1-propyl) nicotinic amidoxime or an acid additional salt thereof.

4. A method for the treatment of a disease selected from the group consisting of cardimyopathy and amyotropric lateral sclerosis, which comprises administering an effective non-toxic does to a patient suffering from said disease of an amidoximic acid derivative of formula I

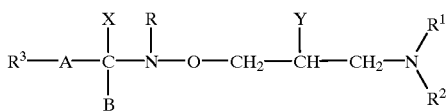

wherein
$R^1$ represents a hydrogen atom or $C_{1-5}$ alkyl group,
$R^2$ represents a for a hydrogen atom, $C_{1-5}$ alkyl group, a $C_{5-7}$ cycloalky group or a phenyl group optionally substituted by a hydroxy or a phenyl group, or
$R^1$ and $R^2$ together with the nitrogen atom they are attached to for a 5 to 8 membered ring optionally containing one ore more further nitrogen or oxygen atom(s) and said ring can be condensed with a benzene ring,
$R^3$ represents a hydrogen atom, a phenyl group, a naphthyl group or a pyridyl group wherein said groups can be substituted by one or more halo atom(s) or $C_{1-4}$ alkoxy groups(s),
Y is a hydroxy group,
X represents an amino group,
R forms with B a chemical bond,
A is a group of the formula b

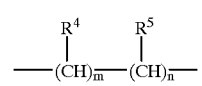

wherein
$R^4$ represents a hydrogen atom,
$R^5$ represents a hydrogen atom,
m has a value of 0, 1 or 2,
n has a value of 0, 1 or 2, or a pharmaceutically acceptable acid addition salt thereof.

5. The method of claim 4, wherein $R^1$ and $R^2$ together with a nitrogen atom are attached to form a piperidino group.

6. The method of claim 4, wherein the hydroximic acid derivative is O-3-poperidino-2-hydroxy-1-propyl)nicotinic amidoxime or an acid additional salt thereof.

7. A method for the treatment of a disease selected from the group consisting of Parkinson's disease and Huntingdon's disease, which comprises administering an effective non-toxic dose to a patient suffering from said disease of an amidoximic acid derivative of formula I

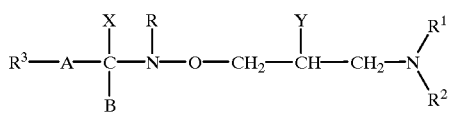

wherein
$R^1$ represents a hydrogen atom or a $C_{1-5}$ alkyl group,
$R^2$ represents for a hydrogen atom, a $C_{1-5}$ alkyl group, a $C_{5-7}$ cycloalkyl group or a phenyl group optionally substituted by a hydroxy or a phenyl group, or
$R^1$ and $R^2$ together with the nitrogen atom they are attached for form a 5 to 8 membered ring optionally containing one or more further nitrogen or oxygen atom(s) and said ring can be condensed with a benzene ring,
$R^3$ represents a hydrogen atom, a phenyl group, a naphthyl group or a pyridyl group wherein said groups can be substituted by one ore more halo atom(s) or $C_{1-4}$ alkoxy group(s),
Y is a hydroxy group,
X represents an amino group,
R forms with B a chemical bond, A is a group of the formula b
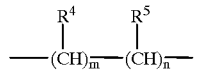
wherein
$R^4$ represents a hydrogen atom,
$R^5$ represents a hydrogen atom,
m has a value of 0, 1 or 2,
n has a value of 0, 1 or 2, or a pharmaceutically acceptable acid addition salt thereof.

UNITED STATES PATENT AND TRADEMARK OFFICE
CERTIFICATE OF CORRECTION

PATENT NO. : 6,306,878 B1
DATED : October 23, 2001
INVENTOR(S) : Sumegi et al.

It is certified that error appears in the above-identified patent and that said Letters Patent is hereby corrected as shown below:

Title page,
Please insert the following -- [73] Assignee: N-Gene Research Labortories, Inc., New York, NY (USA) --.

Signed and Sealed this

Twelfth Day of February, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.      : 6,306,878 B1
DATED           : October 23, 2001
INVENTOR(S)     : Balazs Sumegi et al.

It is certified that error appears in the above-identified patent and that said Letters Patent is hereby corrected as shown below:

Column 13,
Line 43, change "piperidiono" to -- piperidino --.
Line 49, change "cardimyopathy and amyotropric" to -- cardiomyopathy and amyotrophic --.

Column 14,
Lines 36-37, change "Huntingdon's" to -- Huntington's --.

Signed and Sealed this

Twentieth Day of May, 2003

JAMES E. ROGAN
*Director of the United States Patent and Trademark Office*